(12) United States Patent
Pelletier et al.

(10) Patent No.: US 9,778,172 B2
(45) Date of Patent: *Oct. 3, 2017

(54) PULSE WIDTH MODULATION OF CONTINUUM SOURCES FOR DETERMINATION OF CHEMICAL COMPOSITION

(71) Applicant: Halliburton Energy Services, Inc., Houston, TX (US)

(72) Inventors: Michael Pelletier, Houston, TX (US); William Soltmann, The Woodlands, TX (US); David L. Perkins, The Woodlands, TX (US); Christopher M. Jones, Houston, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/385,482

(22) Filed: Dec. 20, 2016

(65) Prior Publication Data

US 2017/0102320 A1 Apr. 13, 2017

Related U.S. Application Data

(62) Division of application No. 14/441,484, filed as application No. PCT/US2012/072194 on Dec. 28, 2012, now Pat. No. 9,523,636.

(51) Int. Cl.
*G01N 21/25* (2006.01)
*H05B 37/02* (2006.01)
(Continued)

(52) U.S. Cl.
CPC ............ *G01N 21/255* (2013.01); *G01J 3/027* (2013.01); *G01J 3/108* (2013.01); *G01J 3/427* (2013.01);
(Continued)

(58) Field of Classification Search
CPC ..... G01J 1/08; G01N 21/59; G01N 2201/022; G01N 2201/061; G01V 8/12
(Continued)

(56) References Cited

U.S. PATENT DOCUMENTS 3,826,920 A 7/1974 Woodroffe et al.
4,907,895 A 3/1990 Everest
(Continued)

FOREIGN PATENT DOCUMENTS

EP 2320213 A2 5/2011
JP 2002365217 A 12/2002
(Continued)

OTHER PUBLICATIONS

International Search Report and the Written Opinion of the International Searching Authority, or the Declaration, dated Sep. 27, 2013, PCT/US2012/072194, 14 pages, ISA/KR.
(Continued)

*Primary Examiner* — Sang Nguyen
(74) *Attorney, Agent, or Firm* — Haynes & Boone, LLP (57) ABSTRACT

A light source and a method for its use in an optical sensor are provided, the light source including a resistively heated element. The light source includes a power circuit configured to provide a pulse width modulated voltage to the resistively heated element, the pulse width modulated voltage including: a duty cycle with a first voltage; and a pulse period including a period with a second voltage, wherein: the duty cycle, the first voltage, and the pulse period are selected so that the resistively heated element is heated to a first temperature; and the first temperature is selected to emit black body radiation in a continuum spectral range. Also provided is an optical sensor for determining a chemical composition including a light source as above.

8 Claims, 8 Drawing Sheets

(51) Int. Cl.
*G01J 3/02* (2006.01)
*G01J 3/10* (2006.01)
*G01J 3/427* (2006.01)
*G01J 3/433* (2006.01)
*G01J 5/52* (2006.01)
*G01N 21/31* (2006.01)

(52) U.S. Cl.
CPC .............. *G01J 3/433* (2013.01); *G01J 5/522* (2013.01); *G01N 21/31* (2013.01); *H05B 37/0209* (2013.01); *G01N 2201/0696* (2013.01); *G01N 2201/06186* (2013.01)

(58) Field of Classification Search
USPC .............. 356/432–444; 250/269.1, 277.11, 250/214 DC, 208.2, 504 R
See application file for complete search history.

(56) References Cited

U.S. PATENT DOCUMENTS

| | | |
|---|---|---|
| 5,026,992 A | 6/1991 | Wong |
| 5,141,312 A | 8/1992 | Thompson et al. |
| 5,388,909 A | 2/1995 | Johnson et al. |
| 5,591,975 A | 1/1997 | Jack et al. |
| 5,621,521 A | 4/1997 | Takahashi |
| 6,400,449 B2 | 6/2002 | Maris et al. |
| 6,404,494 B1 | 6/2002 | Masonis et al. |
| 7,301,164 B2 | 11/2007 | Daugherty et al. |
| 7,372,031 B2 | 5/2008 | Cerwin et al. |
| 7,796,263 B2 | 9/2010 | Csutak |
| 7,968,848 B2 | 6/2011 | Johnson et al. |
| 8,038,947 B2 | 10/2011 | Thompson |
| 2003/0178578 A1 | 9/2003 | Rao et al. |
| 2004/0239243 A1* | 12/2004 | Roberts ............ B60L 1/14 313/512 |
| 2004/0256995 A1* | 12/2004 | Takeuchi ............ B82Y 10/00 315/169.1 |
| 2006/0125420 A1* | 6/2006 | Boone ............ A61L 9/03 315/291 |
| 2007/0049809 A1 | 3/2007 | Bechtel et al. |
| 2007/0279636 A1 | 12/2007 | Li et al. |
| 2009/0009769 A1* | 1/2009 | Uber ............ G01N 21/1702 356/437 |
| 2010/0117667 A1 | 5/2010 | Lo |
| 2011/0108720 A1 | 5/2011 | Ford et al. |
| 2011/0184678 A1 | 7/2011 | Lee et al. |
| 2011/0216311 A1 | 9/2011 | Kachanov et al. |
| 2012/0228502 A1 | 9/2012 | Willis et al. |

FOREIGN PATENT DOCUMENTS

| | | |
|---|---|---|
| WO | WO 2007/064370 A2 | 6/2007 |
| WO | WO 2009/005799 A1 | 1/2009 |

OTHER PUBLICATIONS

Partial Search Report issued for European Patent Application No. 12890899, dated Jun. 30, 2016, 8 pages.

\* cited by examiner

FIG. 7

PULSE WIDTH MODULATION OF CONTINUUM SOURCES FOR DETERMINATION OF CHEMICAL COMPOSITION

The present application is a divisional of U.S. patent application Ser. No. 14/441,484, filed on May 7, 2015, which is a U.S. National Stage patent application of International Patent Application No. PCT/US2012/072194, filed on Dec. 28, 2012, the benefits of which are claimed and the disclosures of which are incorporated herein by reference in their entirety.

BACKGROUND

1. Technical Field

Embodiments disclosed herein relate to the field of optical sensors. More particularly, embodiments disclosed herein are related to the field of modulated sources for optical sensors to measure the chemical composition in fluids.

2. Description of Related Art

Optical sensors typically use a light source to provide the excitation of atoms or molecules for prediction or detection of chemical constituents contained in the liquid, solid, or gases under examination. The light source is provided as part of the system or sensor used to study these materials and generally cover a portion, or portions, of the electromagnetic spectral region from the ultraviolet (UV) to the far infrared (FIR). Different types of light sources used may provide a continuum emission, line emission, and continuum plus line and quasi-continuum emission, according to the spectral distribution of the light provided. Examples of these types of sources are incandescent lamps, hollow cathode discharge lamps, xenon-mercury arc lamps, light emitting diodes (LEDs) and lasers, respectively.

Typically, continuum sources like tungsten lamps are operated at a fixed, continuous voltage, or current. In typical systems, the detected signal is derived from modulating the light beam with the use of an optical chopper or similar device. Light beam modulation improves the measurements made with these devices by moving the detected signal from a direct current (DC) domain to the alternating current (AC) domain, improving signal drift over time.

An alternative approach is to utilize modulation of the light source itself, without the use of external elements such as optical choppers or modulators. Current systems that modulate light sources typically include semiconductor light sources. In some applications, a modulated current is applied to a semiconductor light source having an emitter. The current modulation produces a temperature modulation in a gain region of the emitter, thus changing the emitted center wavelength. This method has been used to measure properties of a downhole fluid in oil exploration and extraction applications. However, light source modulation methods such as used in state-of-the-art applications include light sources providing a limited bandwidth such as lasers and semiconductor light sources, typically emitting light within a narrow wavelength band.

What is needed is an optical source and a method for using the optical source providing measurement stability and high signal-to-noise (SNR) ratio in a broad spectral band, to determine the chemical composition of fluids including hydrocarbons (e.g., crude oils, natural gas, or the like) and/or other fluids present in a downhole environment.

BRIEF SUMMARY

A light source for use in an optical sensor according to some embodiments may include a resistively heated element; and a power circuit configured to provide a pulse width modulated voltage to the resistively heated element, the pulse width modulated voltage including: a duty cycle with a first voltage; and a pulse period including a period with a second voltage, wherein: the duty cycle, the first voltage, and the pulse period are selected so that the resistively heated element is heated to a first temperature; and the first temperature is selected to emit black body radiation in a continuum spectral range.

According to some embodiments an optical sensor for determining a chemical composition of a sample may include: a light source including a resistively heated element; a power circuit configured to provide a pulse width modulated voltage signal to the resistively heated element; an optical delivery system to direct an illumination light to a sample; a sample cavity containing the sample and configured to receive the illumination light; an optical collection system to collect a sample light from the sample; and a detector synchronized to the pulse width modulated voltage signal, the detector configured to measure the sample light from the optical collection system.

According to embodiments disclosed herein a method of determining a chemical composition of a sample using an optical sensor may include: generating an illumination light using a pulse width modulated voltage; collecting a sample light; measuring the sample light with a detector; and determining a chemical component in the sample; wherein the pulse width modulated voltage includes a plurality of pulses having a first frequency, and a duty cycle.

These and other embodiments will be described in further detail below, with reference to the following drawings.

BRIEF DESCRIPTION OF THE DRAWINGS

Wherever possible, the same reference numbers are used throughout the drawings to refer to the same or like elements.

DETAILED DESCRIPTION

Optical sensors consistent with this disclosure are used to determine the chemical composition of a sample of interest. Embodiments of an optical sensor as described herein include a high frequency pulsed-width modulation of a continuum source, to improve sensor performance. For determination of the chemical composition of a sample, use of a continuum light source having a broad spectral band is desirable. A broad spectral band may include visible (VIS) wavelengths from close to the UV region (380-400 nm to about 750 nm), to the near infrared region (NIR, from 750 nm to about 2500 nm), and the mid-infrared region (MIR, from about 2500 nm up to 10 µm and beyond).

Many chemical substances have characteristic optical responses across these three spectral regions (UV-VIS, NIR, and MIR). An optical response from a chemical substance may be obtained by scattering phenomena such as Raman, Brillouin, or Rayleigh scattering, absorption phenomena such as VIS or NIR absorption, or an absorption/emission phenomenon such as fluorescence. Using a broad band light source allows the measurement of many different chemical components, even when they are combined in the same sample. Furthermore, use of a broad band light source may enable the combination of a plurality of phenomena for measurements in different spectral regions. For example, fluorescence spectroscopy may be used in the VIS, Raman spectroscopy may be used in the NIR, and absorption spectroscopy may be used in the MIR. Thus, according to some embodiments, all the above measurement techniques may be applied using the same broadband light source.

Some embodiments of optical sensors as disclosed herein provide a pulse width modulation to a voltage signal, i.e. a pulse width modulated voltage, generating a current in an electrically resistive element of a continuum light source. The pulse width modulation may be provided at a relatively high frequency of several kilo-Hertz (kHz), such as 10 kHz, or more. A continuum light source using a resistive element may be a tungsten filament lamp. In addition to a high frequency modulation of the light source, some embodiments include a lower frequency modulation to the optical beam generated by the lamp. For example, a low frequency modulation may be obtained by using an optical chopper placed in the optical path of a light beam from the lamp, producing a beam modulation of a few hundred Hz, or less.

Figure 1:
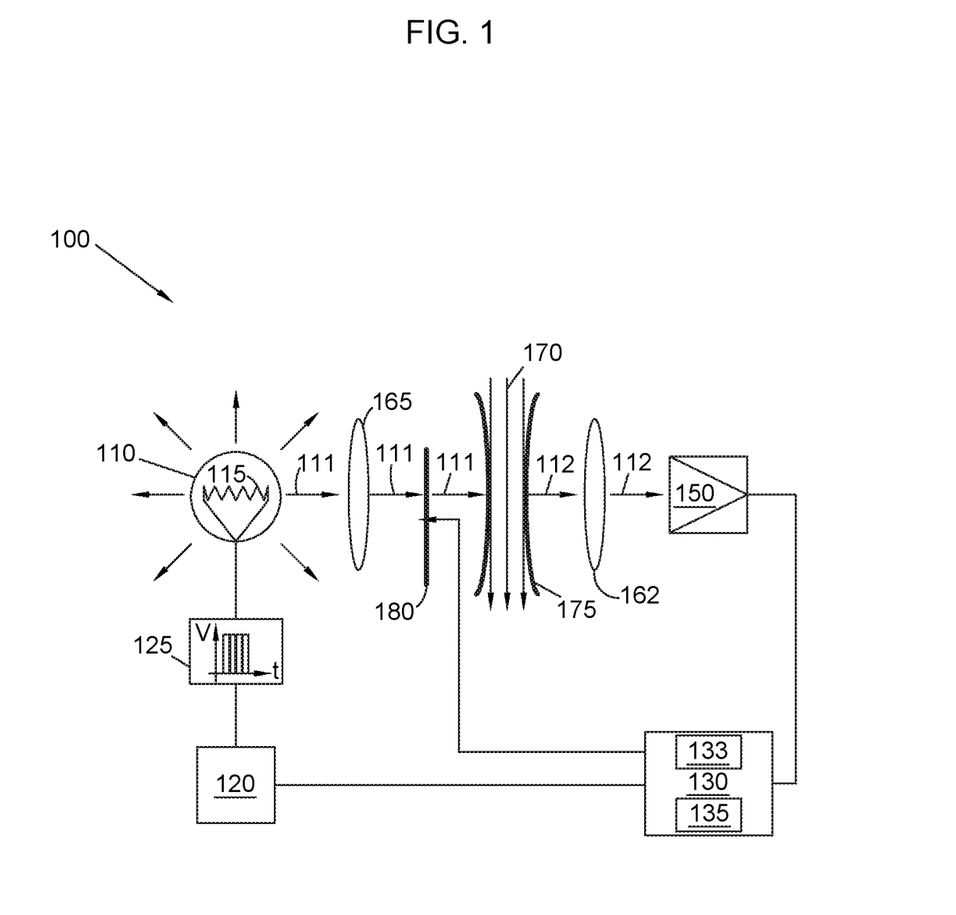
FIG. 1 shows an optical sensor including a modulated optical source, according to some embodiments.

FIG. 1 shows an optical sensor 100 including a modulated light source 110, according to some embodiments. Optical sensor 100 includes a power circuit 120 providing a voltage signal 125 to light source 110. According to some embodiments, voltage signal 125 is a pulse width modulated voltage signal. Light source 110 provides an illumination light 111 upon receiving voltage signal 125. In some embodiments, light source 110 includes a resistively heated element 115. Resistively heated element 115 may be a filament which, upon receiving voltage signal 125, allows a current flow that resistively heats filament 115 up to a temperature $T_0$. The heated filament 115 has a black body emissivity, $\epsilon$, desirably close to 1. In some embodiments, filament 115 is made of an electrically conductive material such as tungsten, and has an emissivity between 0.03 and up to 0.35. The spectral band of the electromagnetic radiation emitted by filament 115 may be selected according to the Planck distribution for a black body at temperature $T_0$. Thus, by selecting the temperature $T_0$, a continuum spectral range including the VIS, NIR, and MIR regions may be obtained at desired emission intensity.

Optical sensor 100 also includes an optical delivery system 165 to collect a portion of the radiation emitted by filament 115 in light source 110 and to form a collimated beam for delivery of illumination light 111 to a sample 170. Sample 170 may be flowing continuously through a sample cavity 175, or may be extracted and stored within sample cavity 175. While the arrows in sample 170 indicate a flow, in some embodiments sample 170 may be stationary within an enclosed cavity 175. In some embodiments, sample cavity 175 may have at least one portion or window transparent to illumination light 111. Thus, sample cavity 175 may include at least one portion or window transparent to wavelengths of interest for the measurement. An optical modulator 180 may be placed in the path of the collimated beam, before illumination light 111 interacts with sample 170. After illumination light 111 interacts with sample 170, optical collection system 162 collects a sample light 112. Optical collection system 162 provides sample light 112 to detector 150 which produces a signal. Optical sensor 100 may also include controller 130 having a processor circuit 133 and a memory circuit 135. Controller 130 performs signal processing, data analysis and data storage using the signal provided by detector 150, processing circuit 133, and memory circuit 135.

In some embodiments, light source 110 in optical sensor 100 may be a tungsten light source. More generally, light source 110 may be a blackbody continuum source using an electrically resistive element emitting light in a broad spectral band. Light source 110 in optical sensor 100 using pulse width modulated signal 125 may operate at an increased temperature relative to a light source operating at a constant voltage, since the stress induced by a high current in filament 115 is reduced by pulsed width modulated signal 125. An increased operation temperature is desirable to increase output intensity of an optical source, according to Planck's law. Intensity increase at longer wavelengths is particularly desirable, since traditional sources have low intensity in the spectral region beyond 2000 nm. Because of the lower stress to filament 115 under pulse width modulated signal 125, light source 110 has an improved performance in terms of stability. Due to the increased optical intensity at any given wavelength, light source 110 improves SNR in detector 150. Improved stability of light source 110 and higher SNR at detector 150 enhance accuracy and precision of a sample chemical composition determined by optical sensor 100.

In some embodiments the signal from detector 150 is demodulated in controller 130 at a frequency approximately equal to a sum or a difference frequency of the voltage modulation frequency provided to filament 115 (f1) and the modulation frequency of the optical modulator, or second frequency f2. In cases where detector 150 is a cascaded voltage detector, the detector may be synchronized to a combination frequency including a sum or a difference of the first frequency (f1) and the second frequency (f2).

In addition, embodiments of optical sensor 100 powered with a battery provide a longer battery lifetime, due to low current usage by pulse width modulated signal 125. For measurement stations using optical sensor 100 in field applications, low current usage results in longer time on station and more measurements between battery charging and/or replacement.

Figure 2:
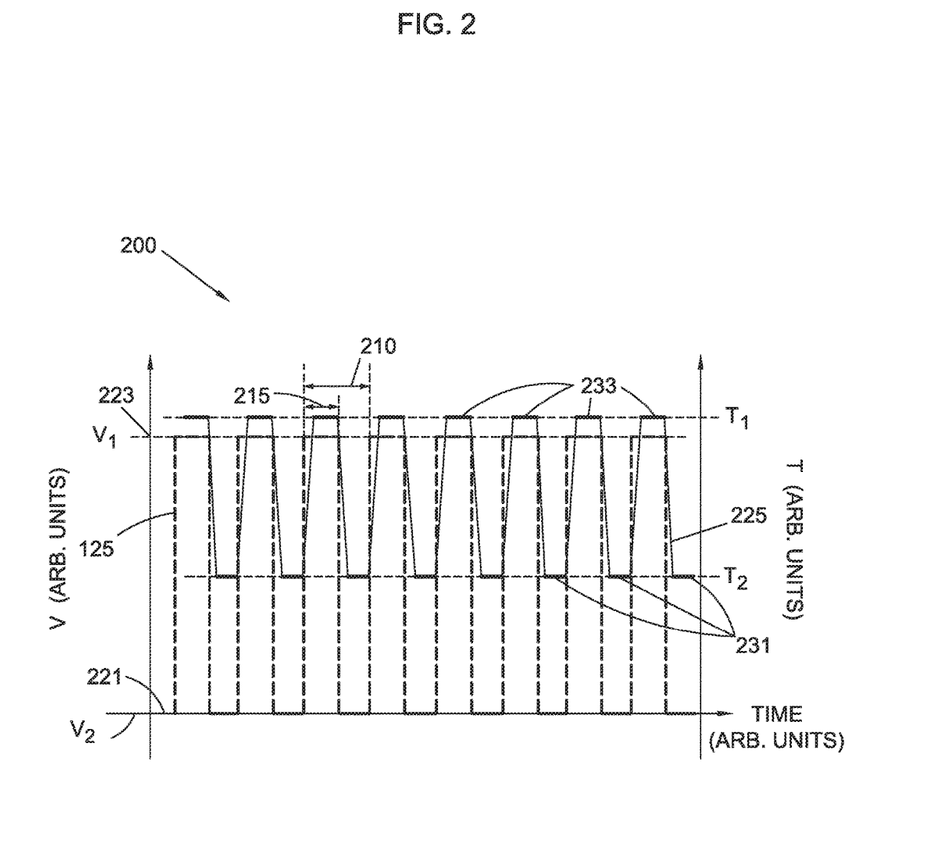
FIG. 2 shows a chart including a pulse modulated signal provided to an optical source, according to some embodiments.

FIG. 2 shows a chart 200 including pulse width modulated signal 125 provided to an optical source, according to some embodiments. The abscissa in chart 200 corresponds to time, the ordinate in the left hand axis is voltage, and the ordinate in the right hand axis is temperature. Chart 200 includes pulse width modulated signal 125, plotted in relation to the voltage axis (ordinate to the left), and a filament temperature curve 225 (ordinate to the right). According to some embodiments, pulse width modulated signal 125 has a period 210 and a duty cycle 215. Duty cycle 215 includes the time during which lamp filament 115 is turned 'on' at a voltage 223 $V_1$. Outside of duty cycle 215, filament 115 may be turned 'off' completely (0 voltage), or may be turned 'on' at a low voltage 221 ($V_2$).

Filament temperature curve 225 includes time segments 233 at a high temperature $T_1$, and time segments 231 at a low temperature $T_2$. Time segments 233 may overlap at least in part with duty cycle 215 of filament 115. Indeed, when filament 115 is operated at voltage 223 ($V_1$), a current resistively heats filament 115 to temperature $T_1$. The heating process may include a small time delay, as thermal equilibrium is reached in filament 115. This time delay is shown in FIG. 2 as a small displacement of time segments 233 to the right relative to voltage pulses, along the abscissa. Likewise, time segments 231 approximately overlap with portions of signal 125 where voltage 221 applied to filament 115 is zero, or low. When the voltage applied to filament 115 is zero or low, no current or a very limited amount of current flows through filament 115. The result is a cooling of the filament down to temperature $T_2$, as the resistive heating stops.

In some embodiments, voltage 223 ($V_1$) may be approximately 20 V, with a duty cycle 215 of approximately 1.5 μs and a period 210 of approximately 100 μs (switching frequency of 10 kHz). In such embodiments, time segments 233 (approximately 1.5 μs or less) may be much shorter than time segments 231 (approximately 98.5 μs). Thus, light source 110 may have enhanced lifetime and operational stability, since the maximum stress for filament 115 at time segments 233 is reduced and interleaved with limited or no stress at time segments 231.

Duty cycle 215, voltage 221, and pulse period 210 are selected so that filament 115 is heated to high temperature $T_1$. Temperature $T_1$ is selected to emit black body radiation in a continuum spectral range. In some embodiments, it is desirable to obtain a broad continuum spectral band, including the VIS, NIR, and MIR regions up to about 5 μm or more, with high enough emission intensity. In such configurations, it is desirable that temperature $T_1$ be as high as several thousand degrees Kelvin (K). For example, in some embodiments $T_1$ may reach about 2000 K, 3000 K, or up to about 5000 K. Further according to some embodiments, duty cycle 215, voltage 221, and pulse period 210 may be selected so that filament 115 reaches temperature $T_2$. Temperature $T_2$ may be selected to emit blackbody radiation in a second continuum spectral range different from the continuum spectral range emitted by filament 115, at temperature $T_1$. In some embodiments, the continuum spectral range emitted at temperature $T_1$ and the second continuum spectral range emitted at temperature $T_2$ may be used in a differential spectrum configuration to enhance the SNR of the measurement.

In some embodiments, the signal from detector 150 is demodulated in controller 130 at a first frequency (f1) approximately equal to the frequency of pulse width modulated signal 125. In some embodiments, the signal from detector 150 is synchronized in controller 130 with duty cycle 215 in pulse width modulated signal 125. Further according to some embodiments, detector 150 may be a cascaded voltage detector that is turned 'on' synchronously with pulse width modulated signal 125 provided to filament 115. In such embodiments, the SNR of the measurement is increased due to the filtering of low frequency and 1/f1 flicker noise, where f1 is the modulation frequency (i.e., the frequency of the voltage pulses in pulse width modulated signal 125).

Figure 3A:
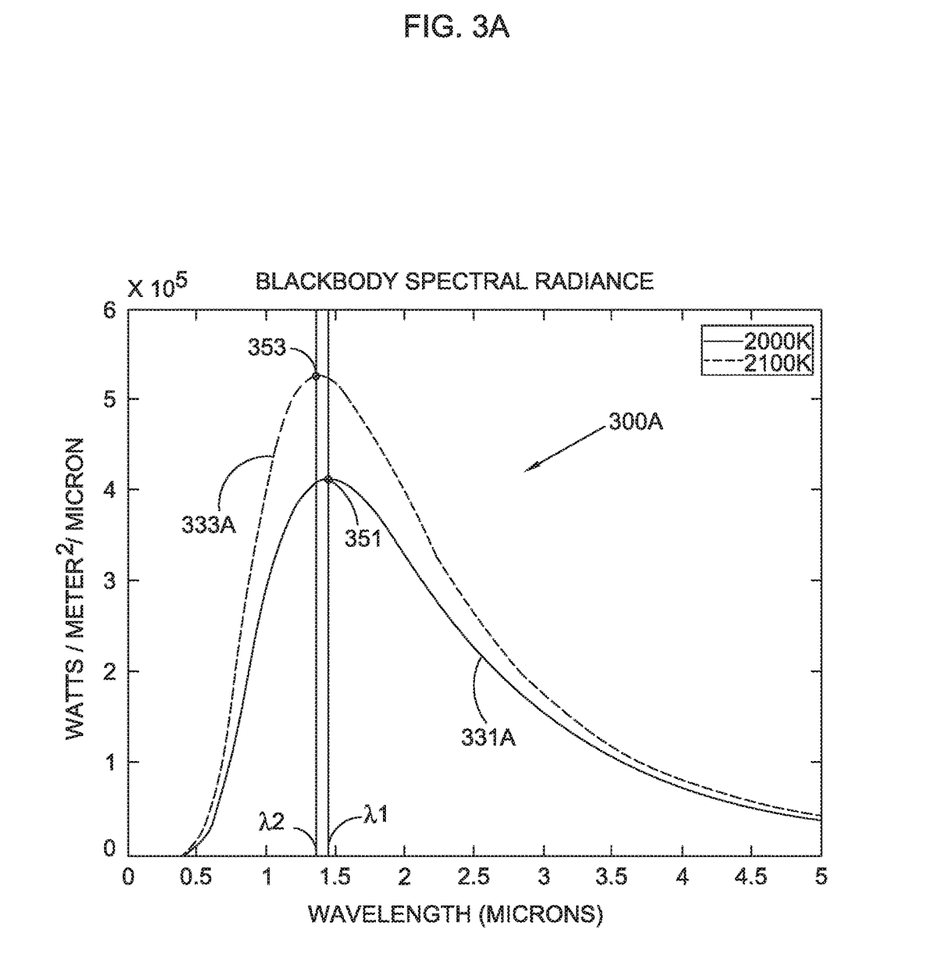
FIG. 3A shows a chart including non-normalized spectral radiance curves at two different temperatures.

FIG. 3A shows a chart 300A including non-normalized spectral radiance curves 331A and 333A. The abscissa axis (X-axis) in FIG. 3A corresponds to wavelength in microns (1 micron=1 μm=$10^{-6}$ m). The ordinate axis (Y-axis) in FIG. 3A is the spectral radiance in Watts per meter squared, per micron. Curve 331A is obtained at a low temperature $T_2$=2000K, and curve 333A is obtained at a high temperature $T_1$=2100 K. The wavelength ranges for curves 331A and 333A are similar, but the overall radiance intensity (ordinate axis, or Y-axis) increases due to the temperature increase. Temperatures $T_1$ and $T_2$ in chart 300A are exemplary only and are not limiting of embodiments consistent with the present disclosure. Accordingly, low temperature $T_2$ may be the filament temperature during a time segment 231, and high temperature $T_1$ may be the filament temperature during a time segment 233, as described in detail above (cf. FIG. 2). FIG. 3A illustrates data point 351 corresponding to a maximal spectral radiance for curve 331A at a wavelength $\lambda_1$. Likewise, data point 353 in curve 333A corresponds to a maximal spectral radiance for curve 333A, at a wavelength $\lambda_2$.

Figure 3B:
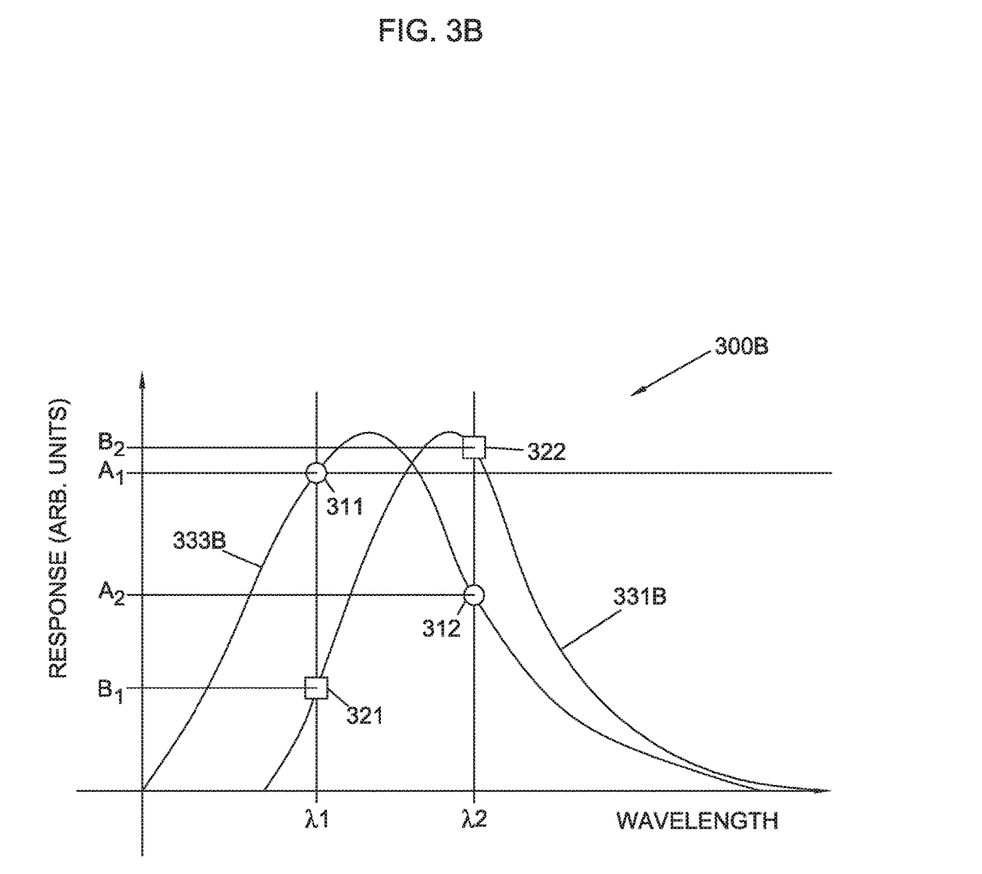
FIG. 3B shows a differential spectrum response from an optical source, according to some embodiments.

FIG. 3B shows a differential spectrum response 300B, according to some embodiments. Differential spectrum response 300B includes a first normalized response curve 331B at a low temperature $T_2$, and a second normalized response curve 333B at a high temperature $T_1$. Low temperature $T_2$ may be the filament temperature during one of the time segments 231, and high temperature $T_1$ may be the filament temperature during one of the time segments 233, as described in detail above (cf. FIG. 2). The first normalized response curve 331B and the second normalized response curve 333B may reflect a spectral distribution of sample light 112 resulting from the interaction of illumination light 111 with sample 170. Response curves 331B and 333B may be normalized to the maximum value of a detector response to sample light 112 across the bandwidth of light source 110. The second response curve 333B at temperature $T_1$ has a signal 311 at wavelength $\lambda_1$ and signal 312 at wavelength $\lambda_2$. The first response curve 331 at temperature $T_2$ has a signal 321 at wavelength $\lambda_1$ and signal 322 at wavelength $\lambda_2$. Signal 311 has a response level $A_1$ and signal 312 has a response level $A_2$. Signal 321 has a response level $B_1$ and signal 322 has a response level $B_2$. Response levels $A_1$, $A_2$, $B_1$, and $B_2$, may be related to signals obtained using a photodetector such as photodetector 150 (cf. FIG. 1).

Response curves 331B and 333B may represent detector signal levels for a plurality of wavelengths within the bandwidth of light source 110. In some embodiments, response curves 331B and 333B may include Raman, Brillouin, Rayleigh, fluorescence, or absorption spectra from the sample. According to some embodiments, a plurality of response curves such as normalized curves 331 and 333 may be stored in memory circuit 135. For example, a normalized response curve may be stored in memory circuit 135 for each of a chemical component that may be found in a sample. Furthermore, for each of the chemical components that may be found in a sample, a plurality of normalized response curves may be stored in memory circuit 135, each corresponding to a different temperature of filament 115 in light source 110.

In a differential spectrum measurement as shown in FIG. 3B, a contrast value is obtained from response signals at two different wavelengths $\lambda_1$ and $\lambda_2$, for a given normalized spectral response curve. In some embodiments, a contrast value may be obtained by subtracting a response value from the spectral response curve at wavelength $\lambda_2$ from a response value from the spectral response curve at wavelength $\lambda_1$. Further, a differential spectrum measurement may use the contrast values from two different spectral response curves to enhance the SNR of a detected signal. For example, a differential spectrum measurement may subtract a contrast value from a first spectral response curve from the contrast value of a second spectral response curve.

As described in FIG. 3B a first spectral response curve may be normalized curve 333B and a first difference contrast value from the response at wavelength $\lambda_2$ and wavelength $\lambda_1$ may be $\Delta A = A_2 - A_1$. A second spectral response curve may be normalized curve 331B, and a second difference contrast value may be $\Delta B = B_2 - B_1$. In such case, a differential spectrum measurement may be $$\delta \Delta = \Delta B - \Delta A \quad (1)$$

If the difference contrast value $\Delta A$ or $\Delta B$ indicates a signal of interest in the sample, then difference $\delta \Delta$ in Eq. (1) results in a greater signal than would be obtained by using the difference contrast value of a single spectral response curve. For example, in FIG. 3B the sign of difference contrast value $\Delta A$ is opposite to the sign of difference contrast value $\Delta B$. Thus, the subtraction in Eq. (1) increases the value of $\delta \Delta$ over the value of both $\Delta A$ and $\Delta B$, increasing the SNR of the measurement. The signal of interest in the sample may be the fractional concentration of a specific chemical component in a fluid. In some embodiments, the signal of interest may be the octane value of a gasoline in a fluid coming from an oil refining process. In some embodiments, the signal of interest may be the fractional water content in a crude oil sample extracted from a downhole drilling tool. Further according to some embodiments, the signal of interest may be the gas-oil-ratio (GOR) in a crude oil sample extracted from a downhole drilling tool.

In some embodiments, a contrast value may be obtained from a ratio of the value of the response curve at wavelength $\lambda_1$ to the value of the response curve at wavelength $\lambda_2$. In such embodiments, a similar analysis leading to an enhanced differential signal $\delta \Delta$ according to Eq. (1) follows from the logarithmic values of a first spectral response curve such as curve 333B and the logarithmic values of a second spectral response curve such as curve 331B. Thus, a ratio $rA = A_2/A_1$ and a ratio $rB = B_2/B_1$ may be enhanced in a differential configuration, by finding $$\delta R = \frac{rB}{rA} = \frac{B_2}{B_1} \cdot \frac{A_1}{A_2} \quad (2)$$

Referring to FIG. 3B, it is seen that $B_2 > B_1$ and $A_1 > A_2$, thus the value of $\delta R$ is greater than $B_2/B_1$, because $A_1 > A_2$. Also, the value of $\delta R$ is greater than $A_2/A_1$ because $\delta R > 1$. Thus, the value of $\delta R$ is greater than both of the ratio contrast values rB and rA. When the ratio contrast value rB or rA is related to a signal of interest for a sample, then a differential spectrum configuration as shown above enhances the SNR of the measurement.

Figure 4:
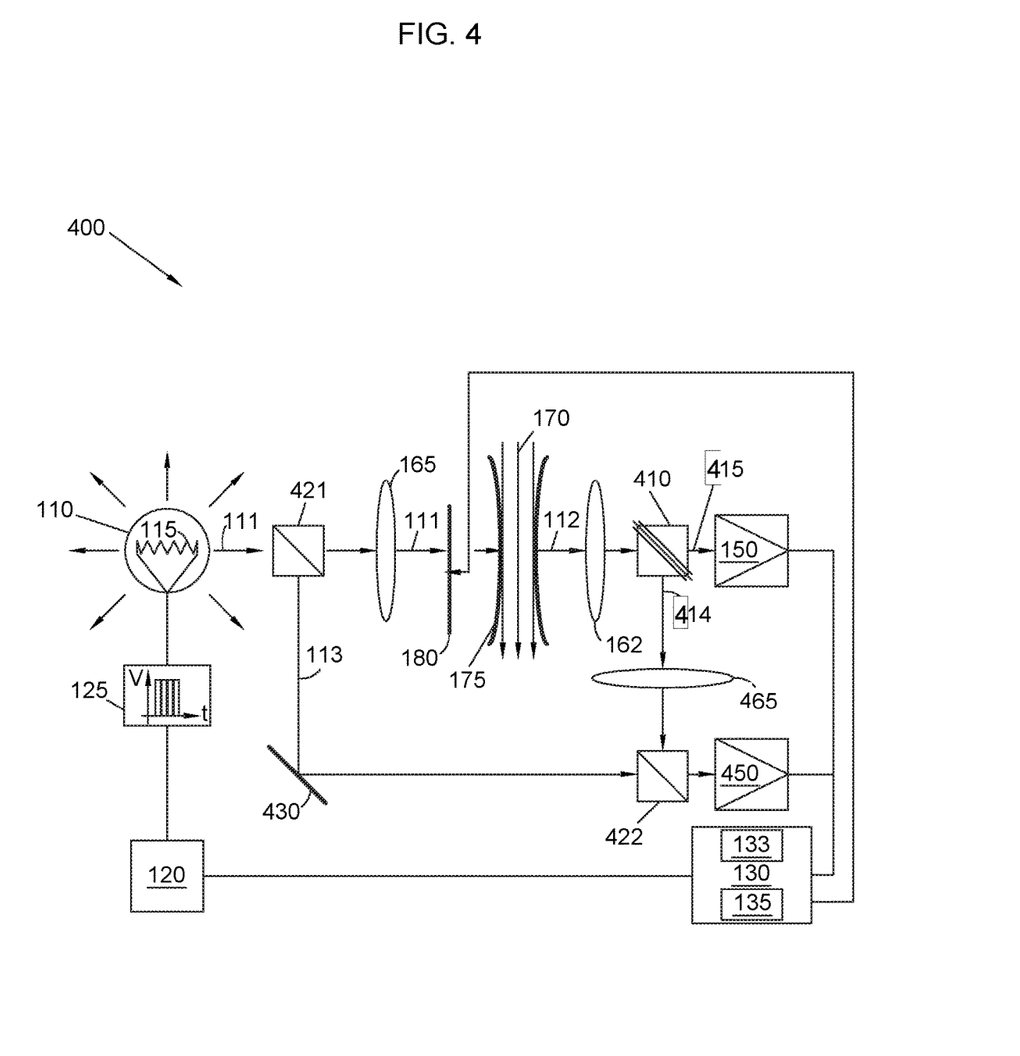
FIG. 4 shows an optical sensor including a modulated optical source and an integrated computational element (ICE), according to some embodiments.

FIG. 4 shows an optical sensor 400 including a modulated light source 110 and an Integrated Computational Element (ICE) 410, according to some embodiments. Optical sensor 400 is similar to optical sensor 100 described in detail above (cf. FIG. 1). Optical sensor 400 includes a reference light detector 450, and an ICE 410 interacting with sample light 112. Reference light detector 450 measures a reference light 113 separated from illumination light 111 by a first beam splitter 421, before illumination light 111 interacts with the sample 170. In some embodiments, reference light 113 is separated from the illumination light 111 before passing through optical modulator 180. Reference light 113 is sent through a second beam splitter 422 towards detector 450 by mirror 430.

One of ordinary skill will recognize that the specific combination of mirror, lenses, and beam splitters in optical sensor 100 (cf. FIG. 1), and in optical sensor 400 is not limiting. Different optical elements well known in the art may be used in a variety of configurations to produce the same effects for collection, collimation, and delivery of light from light source 110, through sample 170, and to detectors 150 and 450. In some embodiments, beam splitters, mirrors, and lenses may be replaced entirely or partially by optical fiber components such as splitters, circulators, and collimators.

ICE 410 modifies and separates sample light 112 into a modified transmitted light 415 and a modified reflected light 414. Modified transmitted light 415 is sent to detector 150. Modified reflected light 414 is collected by optical collection system 465 and sent to detector 450, by second beam splitter 422. In some embodiments, ICE 410 may include a multi-layered dielectric filter that separates sample light 112 into modified reflected portion 415 and modified transmitted portion 415 according to wavelength. Thus, the sum of the intensity of modified reflected portion 414 and the intensity of modified transmitted portion 415 of sample light 112 may be equal to or approximately equal to the intensity of sample light 112. Furthermore, the relative intensity of modified transmitted portion 415 to modified reflected portion 414 of sample light 112 may depend on the chemical composition of sample 170.

In some embodiments, ICE 410 may be selected so that the relative difference between modified reflected portion 414 of the sample light and modified transmitted portion 415 of the sample light is maximized when a certain chemical of interest is present in the sample. In some embodiments, ICE 410 may be designed such that a contrast value is obtained from measuring modified reflected portion 414 and transmitted portion 415 of sample light 112, separately. For example, for a contrast value such as difference contrast values $\Delta A$ and $\Delta B$ (cf. Eq. (1) and FIG. 3), ICE 410 may be selected such that modified transmitted portion 415 includes value $A_1$, and $B_1$, and modified reflected portion 414 includes values $A_2$ and $B_2$. Accordingly, the opposite choice may be selected, e.g., ICE 410 may be selected such that modified transmitted portion 415 includes values $A_2$ and $B_2$, and modified reflected portion 414 includes values $A_1$ and $B_1$. In such embodiments, the difference contrast values $\Delta A$ and $\Delta B$ may be obtained simply by subtracting the signals measured in detectors 150 and 450. In embodiments using a ratio as a contrast value, such as ratio contrast values rA and rB (cf. Eq. (2) and FIG. 3), the contrast value may be obtained by dividing the signals measured in detectors 150 and 450. Signal processing such as subtraction and division of the signals from detectors 150 and 450 is performed in controller 130 by processing circuit 133. Further data processing may include use of lookup tables and reference spectra stored in memory circuit 135.

Figure 5:
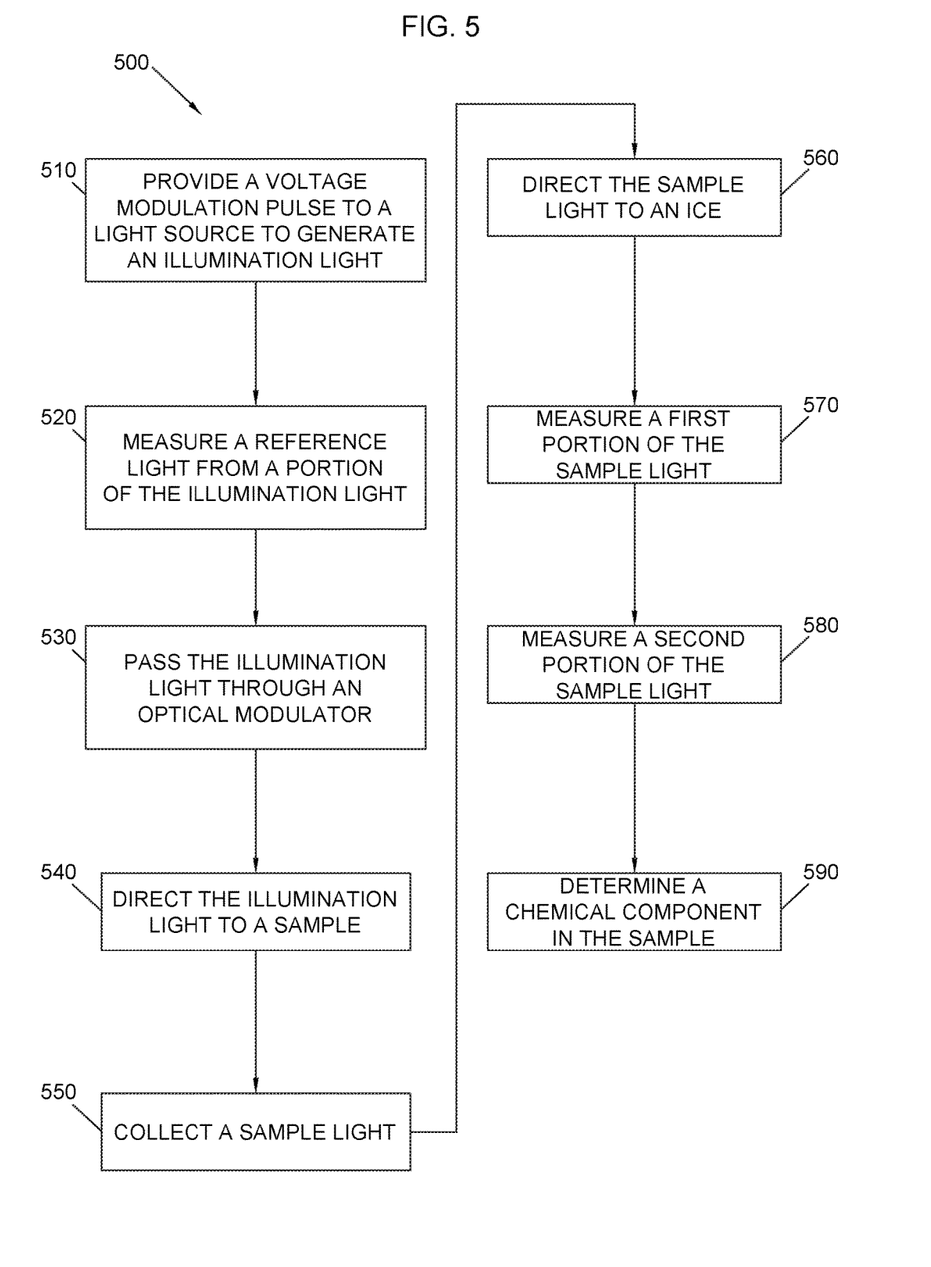
FIG. 5 shows a flow chart for a method to determine chemical composition of a sample using an optical sensor, according to some embodiments.

FIG. 5 shows a flow chart for a method 500 to determine chemical composition of a sample using an optical sensor, according to some embodiments. The optical sensor used in method 500 may be optical sensor 100 or optical sensor 400, described in detail above (cf. FIGS. 1 and 4). Method 500 may be performed by the controller circuit in an optical sensor, such as controller 130 in optical sensor 100 (cf. FIG. 1). The controller circuit may include a processor circuit such as processor circuit 133, to perform operations using commands and data, the commands and data stored in a memory circuit such as memory circuit 135 (cf. FIG. 1). Furthermore, some steps in method 500 may be performed by a power circuit in the optical sensor, such as power circuit 120 in optical sensor 100 (cf. FIG. 1). In some embodiments some steps in method 500 may be performed by power circuit 120 upon receiving commands and signals from the controller circuit.

Step 510 includes providing a voltage modulation pulse to a light source, to generate an illumination light (e.g. illumination light 111, cf. FIG. 1). According to some embodiments, the voltage modulation pulse may be included in a pulse width modulated signal such as pulse width modulated signal 125, provided to filament 115 in light source 110 by power circuit 120. The voltage pulse has a duty cycle such as duty cycle 215 within a period of time such as period 210 (cf. FIG. 2). Thus, in embodiments where a modulation signal such as pulse width modulated signal 125 is provided to light source 110, step 510 may be repeated for a plurality of times while a signal is collected. In some embodiments, the frequency of the pulses provided in step 510 may be approximately 10 kHz, or higher.

Step 520 includes measuring a reference light from a portion of the illumination light. Step 520 may include forming a reference light by splitting a portion of the light emitted by the light source in step 510 with a beam splitter such as beam splitter 421 (cf. FIG. 4). Step 520 may further include reflecting the reference light with a mirror such as mirror 430, and passing the reference light through a beam splitter such as beam splitter 422. Step 520 may also include measuring the reference light with a detector such as detector 450.

Step 530 includes passing the illumination light provided in step 510 through an optical modulator. In some embodiments, step 530 may include collimating the illumination light into a beam using an optical delivery system such as system 165 (cf. FIG. 1). The optical modulator may be optical modulator 180. In some embodiments, the optical modulator may be an optical chopper, operating at a low modulation frequency, compared to the frequency of the pulses provided in step 510. For example, in embodiments where the frequency of the pulses provided in step 510 is about 10 kHz, an optical modulator in step 530 may operate at a frequency of a few hundred Hz, 100 Hz, or even lower.

Step 540 includes directing the illumination light to a sample. The sample in step 540 may be as sample 170 (cf. FIG. 1). The illumination light in step 540 may interact with the sample through scattering phenomena such as Raman, Brillouin or Rayleigh scattering, or an absorption phenomenon such as VIS or NIR absorption. Interaction of the illumination light with the sample in step 540 may also include an absorption and emission phenomenon such as fluorescence emission. Further according to some embodiments, and depending on the chemical composition of the sample, step 540 may include a combination of scattering, absorption, and emission phenomena as described above.

Step 550 includes collecting a sample light. In some embodiments, step 550 may include using an optical collection system such as optical collection system 162 (cf. FIG. 1). Step 560 includes directing the sample light to an ICE, such as ICE 410 described in detail above (cf. FIG. 4). Step 570 includes measuring a first portion of the sample light (e.g., modified transmitted light 415 in FIG. 4). In some embodiments, step 570 includes using a first detector such as detector 150 to measure a first portion of the sample light transmitted through the ICE in step 560. Step 580 includes measuring a second portion of the sample light (e.g., the modified reflected light 414 in FIG. 4) using a second detector, such as detector 450. In some embodiments the second portion of the sample light may be a light reflected from the ICE in step 560. In some embodiments, measuring a first portion and a second portion of the sample light includes synchronizing the two detectors with a duty cycle of the voltage modulation pulse. In some embodiments, measuring a first portion and a second portion of the sample light includes synchronizing the two detectors with a combination frequency including a sum or a difference of the optical modulator frequency and the frequency of the voltage modulation signal.

Step 590 includes determining a chemical component in the sample. According to some embodiments, step 590 may be performed by the controller circuit using a processor circuit and a memory circuit. For example, a controller circuit may use the signals measured in steps 520, 570, and 580 to determine a chemical component in the sample. Furthermore, in step 590 the controller circuit may also use a lookup table or a reference spectrum stored in the memory circuit. Thus, step 590 may include comparing a value obtained from the measured signal to a value stored in a lookup table or in a reference spectrum. Moreover, the memory circuit may store a calibration table, such that a difference between the value obtained from the measured signal and the value stored in the lookup table or the reference spectrum may be converted by the processor circuit into a concentration value for the chemical component in step 590. In some embodiments, step 590 may include use of a multivariate analysis to determine multiple component concentrations in the sample.

In some embodiments, step 590 may include determining whether a certain chemical component is present in the sample or not. In some embodiments, step 590 may further determine the fractional concentration of a chemical component in the sample. The fractional concentration may be a value provided by mass of the sample (e.g., weight percent, % Wt), by volume of the sample (e.g., volume percent, % vol), by molecular counts of the sample (e.g. parts per thousand, million, billion, trillion). In some embodiments, an absolute count of a chemical component may be provided in step 590.

Figure 6:
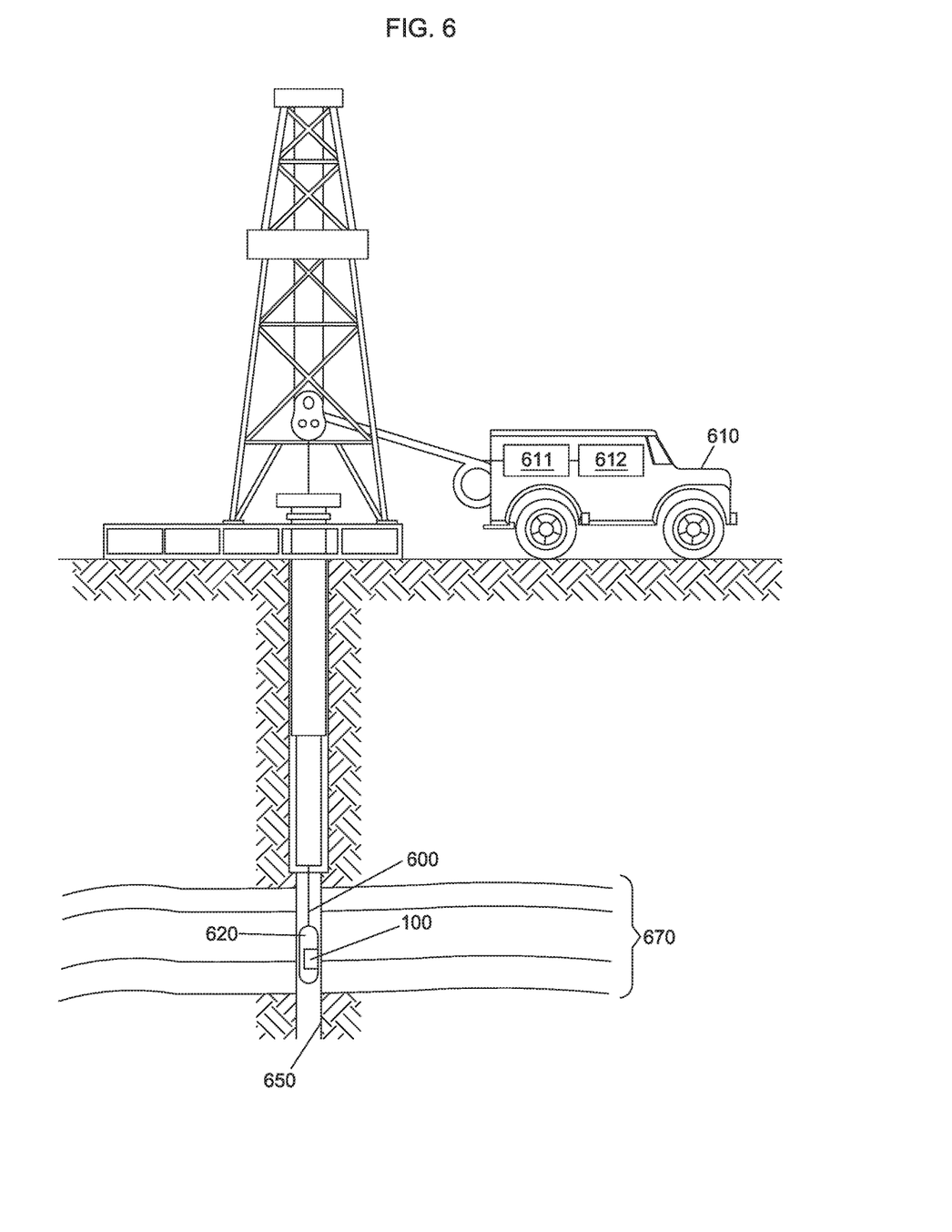
FIG. 6 shows an optical sensor using a modulated optical source in a wireline logging application, according to some embodiments.

FIG. 6 shows an optical sensor 100 using a modulated optical source in a sensor 620 for a wireline logging application, according to some embodiments. Wireline logging performs measurements of fluids and substrates in wellbores drilled for oil and hydrocarbon exploration. In some embodiments, a movable unit 610 includes a processor circuit 611 and a memory circuit 612 to provide commands for sensor 620 to perform measurements and store data obtained from the measurements. Accordingly, once a wellbore 650 has been drilled, a wireline logging measurement may be performed by introducing sensor 620 into wellbore 650, using a wireline 600. Wellbore 650 may traverse through a layered ground formation 670. Sensor 620 may have an optical sensor system 100 including a modulated optical source, as disclosed herein. Furthermore, sensor 620 may include a portion of an optical delivery system such as light delivery system 165 and a portion of an optical collection system such as collection system 162 (cf. FIG. 3). In some embodiments, a portion of light delivery system 165 and an illumination lamp 110 using a modulated optical source, and power circuit 120 may be included in movable unit 610. Likewise, a portion of optical collection system 162 may be included in movable unit 610, such as a detector, an amplifier, and an analog-to-digital converter circuit. In some embodiments, optical delivery system 165 and optical collection system 162 may include an optical fiber, or fiber bundle. The optical fiber or fiber bundle carries light signals along wireline 600.

Figure 7:
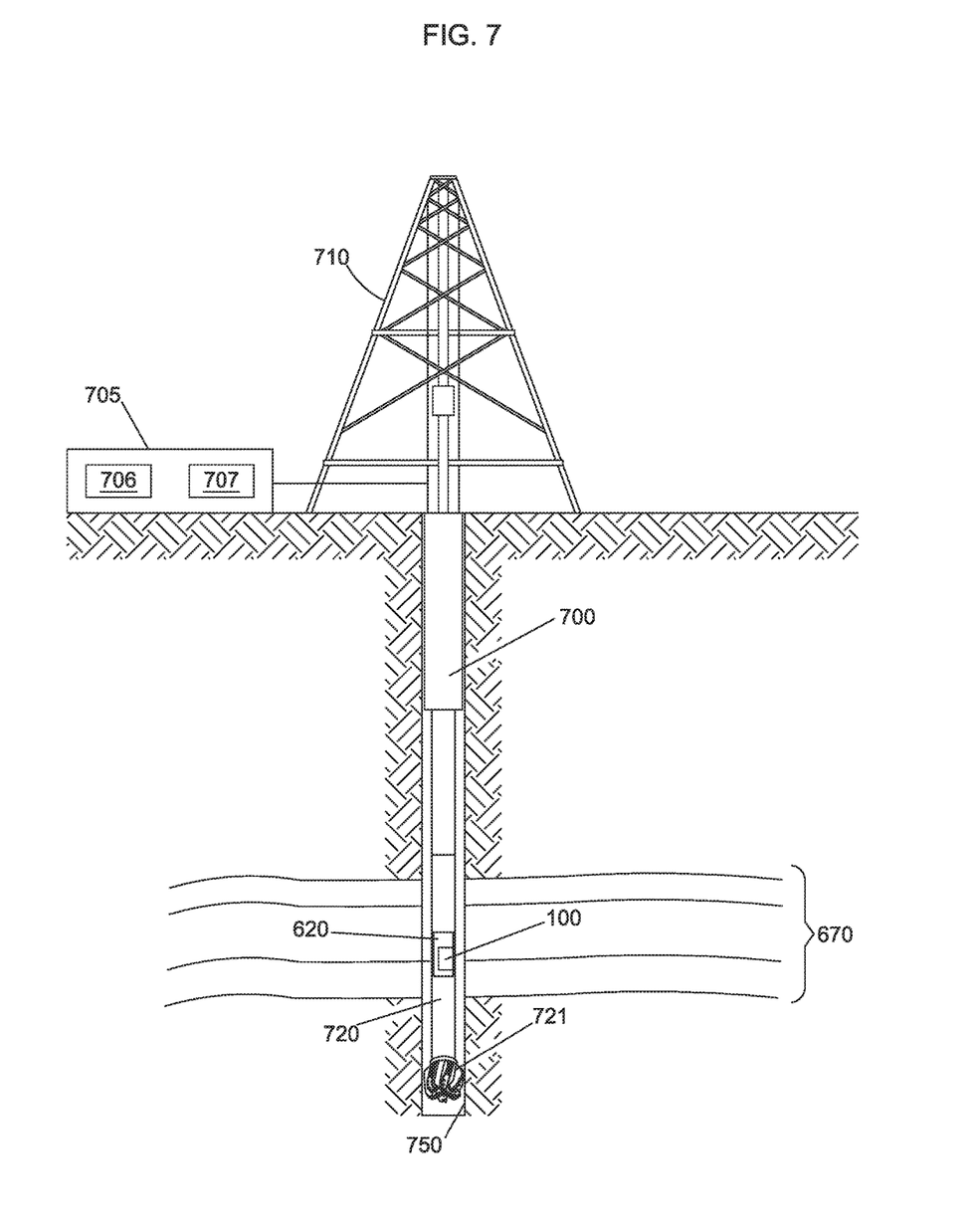
FIG. 7 shows a drill bore including a sensor using a modulated optical source in a logging-while-drilling (LWD) application, according to some embodiments.

FIG. 7 shows a drill bore including an optical sensor 100 using a modulated optical source in a logging-while-drilling (LWD) application, according to some embodiments. An LWD configuration logs acoustic and optical data while a wellbore is being drilled. According to FIG. 7, a bottom hole assembly 720 includes a drill 721 to form a wellbore 750, traversing through layered ground formation 670. Drill 721 may be operated by a controller 705 through drill string 700. A drilling rig 710 provides structural support to drill string 700. Controller 705 may include a processor circuit 706 and a memory circuit 707. Memory circuit 707 stores commands and data used by processor circuit 706 to control bottom hole assembly 720. Controller 705 may also include sensor 620 proximate to drill 721. Sensor 620 may include an optical sensor 100. Sensor 620 may also include a portion of a light illumination system and a portion of a light detection system, as described in detail above (cf. FIG. 6).

In some embodiments, a sensor as disclosed herein may be implemented in permanent monitoring applications. For example, in an oil extraction rig similar to drilling rig 710, optical sensor 100 may determine the chemical composition of the extracted hydrocarbons during regular operations. Further according to some embodiments, an optical sensor such as sensor 100 may be used in a subsea environment of a wireline operation (cf. FIG. 6), an LWD operation (cf. FIG. 7), or a permanent monitoring operation.

Embodiments described herein may provide measurement stability and high SNR ratio in a broad spectral band to more accurately determine the chemical composition of fluids including hydrocarbons such as crude oils, natural gas, and other downhole fluids. Embodiments described herein are exemplary only. One skilled in the art may recognize various alternative embodiments from those specifically disclosed. Those alternative embodiments are also intended to be within the scope of this disclosure. As such, embodiments disclosed herein are limited only by the following claims.

What is claimed is:

1. A light source for use in an optical sensor, the light source comprising:
   a resistively heated element which produces an illumination light;
   an optical modulator that modulates at least a first portion of the illumination light; and
   a power circuit configured to provide a pulse width modulated voltage to the resistively heated element, the pulse width modulated voltage comprising:
   a duty cycle with a first voltage; and
   a pulse period including a period with a second voltage, wherein:
   the duty cycle, the first voltage, and the pulse period are selected so that the resistively heated element is heated to a first temperature; and
   the first temperature is selected to emit black body radiation in a continuum spectral range.

2. The light source of claim 1 wherein the second voltage is lower than the first voltage.

3. The light source of claim 1 wherein the second voltage is zero.

4. The light source of any one of claim 1, 2, or 3 wherein the duty cycle, the second voltage, and the pulse period are selected so that the resistively heated element is heated to a second temperature lower than the first temperature.

5. The light source of claim 4 wherein the second temperature is selected to emit black body radiation in a second continuum spectral range.

6. The light source of claim 1 wherein the illumination light passes through a beam splitter, wherein the splitter splits the illumination light into the first portion and a second portion, and wherein the second portion is output as a reference signal.

7. The light source of claim 6 wherein the second portion is reflected by a mirror prior to being output as the reference signal.

8. The light source of claim 1, further comprising an optical delivery system that collects radiation emitted by the heated element and forms a collimated beam that is the illumination light.

* * * * *